United States Patent
Evgin et al.

(10) Patent No.: US 12,121,554 B2
(45) Date of Patent: Oct. 22, 2024

(54) MATERIALS AND METHODS FOR TREATMENT WITH ONCOLYTIC VIRUSES AND MODIFIED CAR T CELLS

(71) Applicants: Mayo Foundation for Medical Education and Research, Rochester, MN (US); Duke University, Durham, NC (US); Laura Evgin, Rochester, MN (US); Richard G. Vile, Rochester, MN (US); Luis Sanchez-Perez, Apex, NC (US)

(72) Inventors: Laura Evgin, Rochester, MN (US); Richard G. Vile, Rochester, MN (US); Luis Sanchez-Perez, Apex, NC (US)

(73) Assignees: Mayo Foundation for Medical Education and Research, Rochester, MN (US); Duke University, Durham, NC (US)

( * ) Notice: Subject to any disclaimer, the term of this patent is extended or adjusted under 35 U.S.C. 154(b) by 892 days.

(21) Appl. No.: 17/275,713

(22) PCT Filed: Sep. 13, 2019

(86) PCT No.: PCT/US2019/050960
§ 371 (c)(1),
(2) Date: Mar. 12, 2021

(87) PCT Pub. No.: WO2020/056228
PCT Pub. Date: Mar. 19, 2020

(65) Prior Publication Data
US 2021/0275615 A1    Sep. 9, 2021

Related U.S. Application Data

(60) Provisional application No. 62/731,560, filed on Sep. 14, 2018.

(51) Int. Cl.
| | | |
|---|---|---|
| *A61K 35/768* | (2015.01) | |
| *A61K 35/17* | (2015.01) | |
| *C07K 14/705* | (2006.01) | |
| *C07K 14/71* | (2006.01) | |
| *C07K 14/715* | (2006.01) | |
| *C12N 15/86* | (2006.01) | |

(52) U.S. Cl.
CPC ............ *A61K 35/768* (2013.01); *A61K 35/17* (2013.01); *C07K 14/70503* (2013.01); *C07K 14/71* (2013.01); *C07K 14/7156* (2013.01); *C12N 15/86* (2013.01); *C12N 2740/15043* (2013.01); *C12N 2760/20232* (2013.01)

(58) Field of Classification Search
None
See application file for complete search history.

(56) References Cited

U.S. PATENT DOCUMENTS

| | | |
|---|---|---|
| 2013/0251681 A1 | 9/2013 | Russell et al. |
| 2014/0286905 A1 | 9/2014 | Lee |
| 2017/0319638 A1 | 11/2017 | Conner et al. |

FOREIGN PATENT DOCUMENTS

| | | |
|---|---|---|
| WO | WO 2003083065 | 10/2003 |
| WO | WO 2013038066 | 3/2013 |

OTHER PUBLICATIONS

Geoffroy et al. "The pros and cons of interferon for oncolytic virotherapy" (2020), Cytokine and Growth Factor Reviews, vol. 56: 49-58. (Year: 2020).*
Kooti et al. "Oncolytic Viruses and Cancer, Do you Know the Main Mechanism?" (2021), Frontiers in Oncology, vol. 11: 1-11. Article No. 761015. (Year: 2021).*
Guedan et al. "CAR-T Cells and Oncolytic Viruses: Joining Forces to Overcome the Solid Tumor Challeng", (2018), Frontier in Immunology, vol. 9, article No. 2460. (Year: 2018).*
Ajina et al., "Prospects for combined use of oncolytic viruses and CAR T-cells," J. Immunother. Cancer, 5(1):90, Nov. 21, 2017, 27 pages.
Crouse et al., "Type I Interferons Protect T Cells against NK Cell Attack Mediated by the Activating Receptor NCR1," Immunity, 40(6):961-973, Jun. 19, 2014.
EP Extended Search Report in European Appln. No. 19860622.0, dated Nov. 8, 2021, 12 pages.
Evgin et al., "Oncolytic virus-derived type I interferon restricts CAR T cell therapy," Nat. Communications, 11(1):3187, Jun. 24, 2020, 15 pages.
Felt et al., "Recent advances in vesicular stomatitis virus-based oncolytic virotherapy: a 5-year update," J. Gen. Virology, 98(12):2895-2911, Dec. 2017.
Fuertes et al., "Type I interferon response and innate immune sensing of cancer," Trends in Immunology, 34(2):67-73, Feb. 2013.
Metidji et al., "IFN-alpha/beta Receptor Signaling Promotes Regulatory T Cell Development and Function under Stress Conditions," J. Immunology, 194(9):4265-4276, May 2015.
Nishio et al., "Oncolytic virus expressing RANTES and IL-15 enhances function of CAR-modified T cells in solid tumors," Oncoimmunology, 4(2):e988098, Feb. 2015, 3 pages.
Vaha-Koskela et al., "Tumor Restrictions to Oncolytic Virus," Biomedicines, 2(2):163-194, Apr. 17, 2014.
Wing et al., "Improving CART-Cell Therapy of Solid Tumors with Oncolytic Virus-Driven Production of a Bispecific T-cell Engager," Cancer Immunol. Research, 6(5):605-616, May 2018.
Evgin et al., "Unexpected antagonism between oncolytic virus derived type I interferon and EGFRvIII CAR T-cells," Abstract, Presented at Proceedings of the Fourth CRI-CIMT-EATI-AACR International Cancer Immunotherapy Conference: Translating Science into Survival, New York, NY, Sep. 30-Oct. 3, 2018; Cancer Immunol. Research, 7(2S):A029, Feb. 2019.

(Continued)

*Primary Examiner* — Teresa E Knight
(74) *Attorney, Agent, or Firm* — Fish & Richardson P.C.

(57) ABSTRACT

This document relates to methods and materials involved in treating cancer. For example, methods and materials for using one or more oncolytic viruses (OVs) in combination with an adoptive cell therapy (e.g., a chimeric antigen receptor T cell therapy) to alter one or more functions of a T cell and/or to enhance T cell expansion to treat cancer in a mammal (e.g., a human) are provided.

20 Claims, 13 Drawing Sheets

Specification includes a Sequence Listing.

(56) References Cited

OTHER PUBLICATIONS

Gomes-Silva et al., "Tonic 4-1BB Costimulation in Chimeric Antigen Receptors Impedes T Cell Survival and Is Vector-Dependent," Cell Reports, 21(1):17-26, Oct. 2017.
Long et al., "4-1BB costimulation ameliorates T cell exhaustion induced by tonic signaling of chimeric antigen receptors," Nat. Medicine, 21(6):581-590, May 4, 2015.
Obuchi et al., "Development of recombinant vesicular stomatitis viruses that exploit defects in host defense to augment specific oncolytic activity," J. Virology, 77(16):8843-8856, Aug. 2003.
PCT International Preliminary Report on Patentability in International Appln. No. PCT/US2019/050960, dated Mar. 9, 2021, 6 pages.
PCT International Search Report and Written Opinion in International Appln. No. PCT/US2019/050960, dated Nov. 29, 2019, 9 pages.
Rommelfanger et al., "The Efficacy Versus Toxicity Profile of Combination Virotherapy and TLR Agonists to Oncolytic Virus-treated Mice," Am. Soc. Gene Cell Therapy, 21(2):348-357, Feb. 2013.
Stojdl et al., "Exploiting tumor-specific defects in the interferon pathway with a previously unknown oncolytic virus," Nat. Medicine, 6(7):821-825, Jul. 2000.
Willmon et al., "Expression of IFN-beta enhances both efficacy and safety of oncolytic vesicular stomatitis virus for therapy of mesothelioma," Cancer Research, 69(19):7713-7720, Sep. 22, 2009.

\* cited by examiner

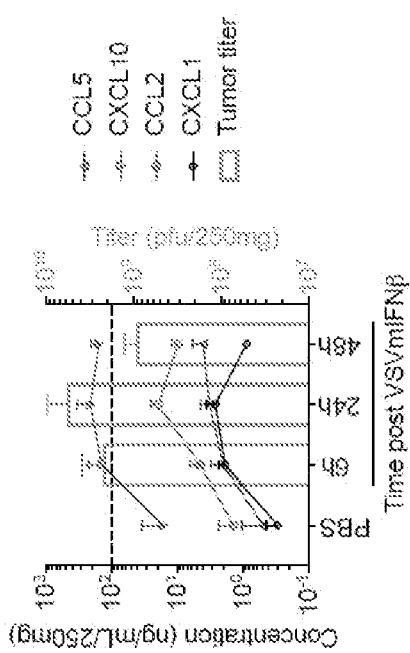
FIG. 1A
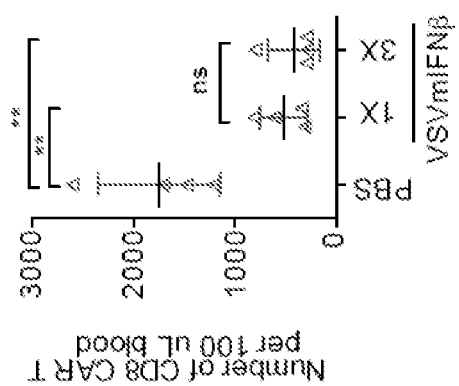
FIG. 1B
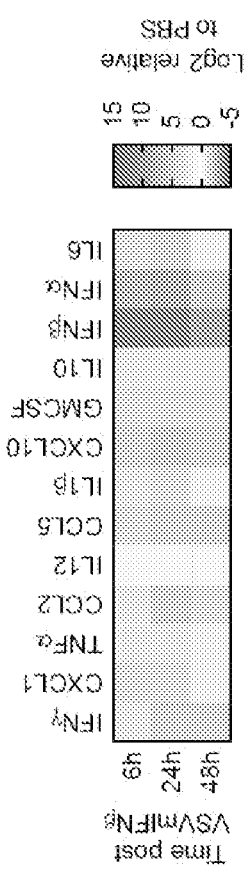
FIG. 1C
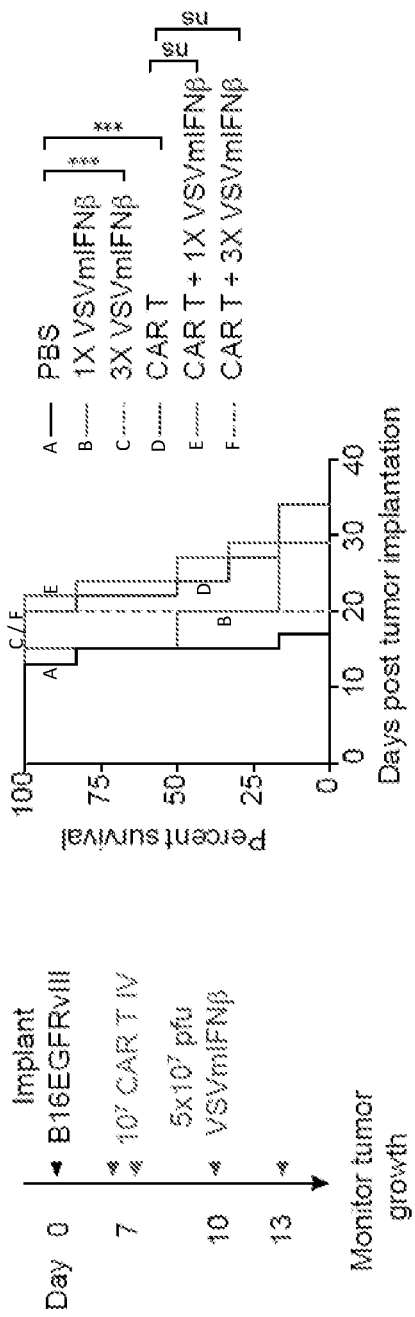
FIG. 1D
FIG. 1E

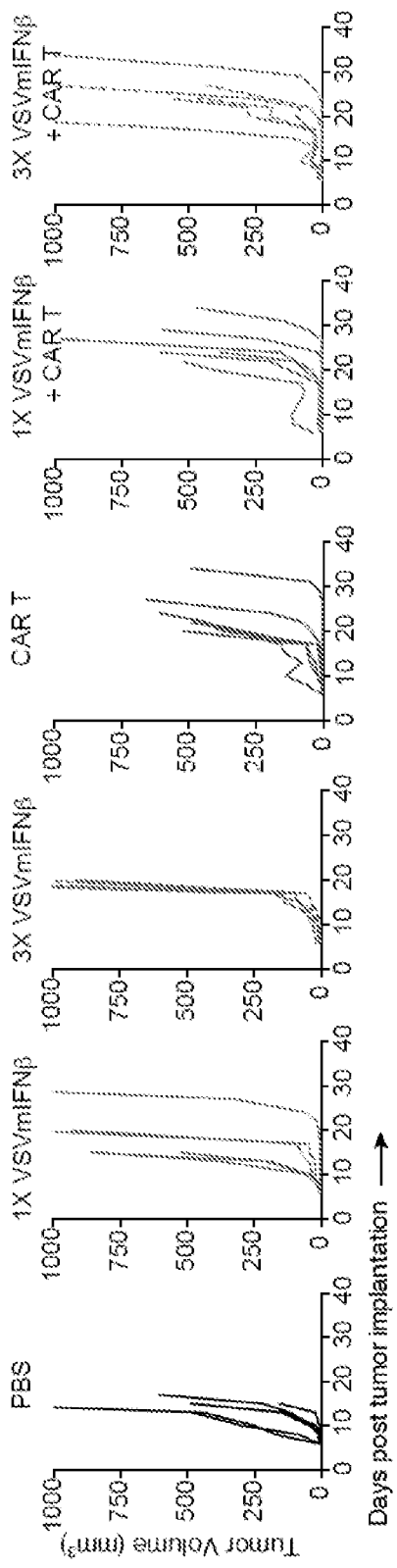
FIG. 1F
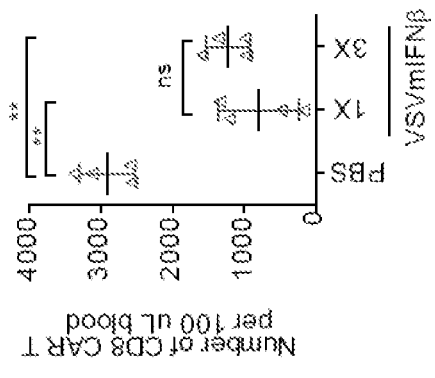
FIG. 1I
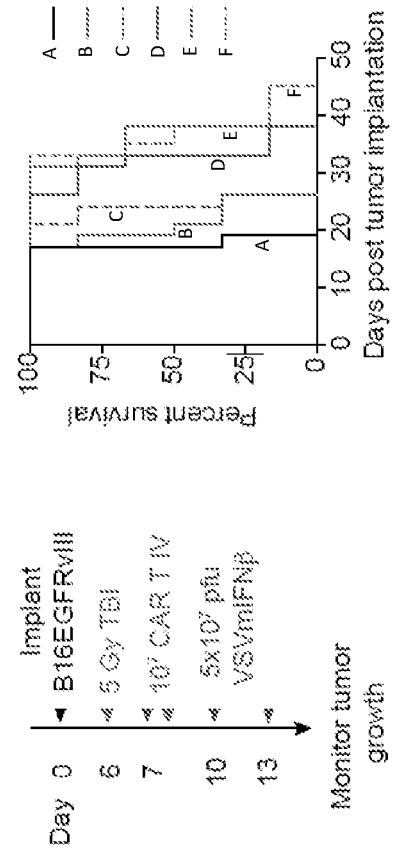
FIG. 1G
FIG. 1H

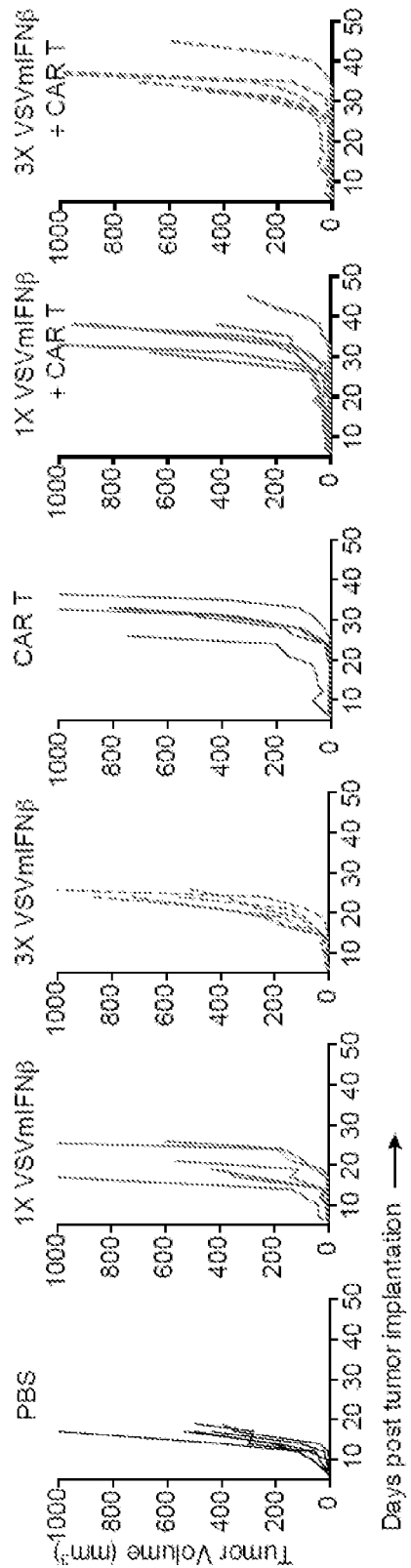

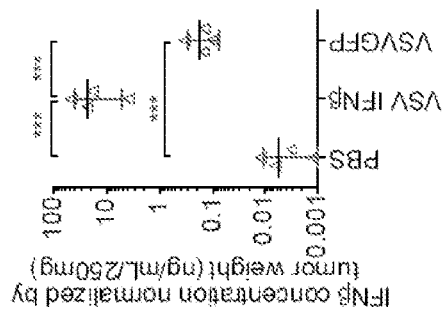
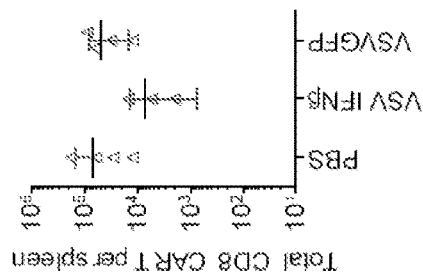
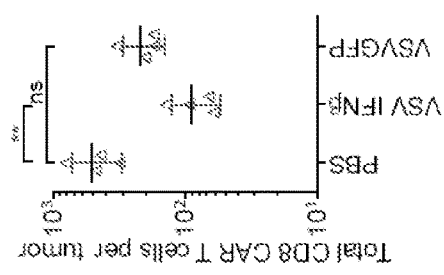
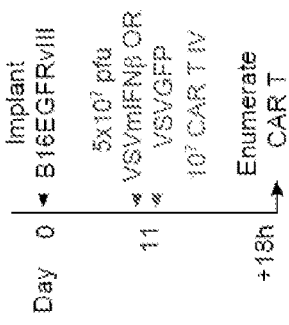
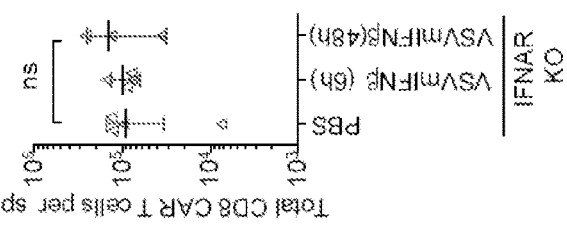
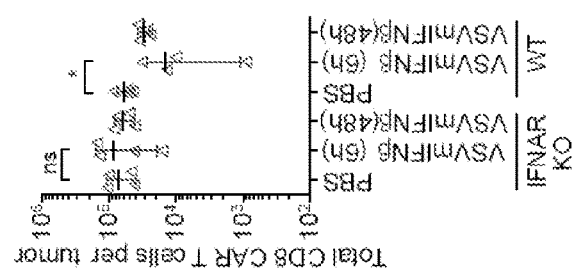
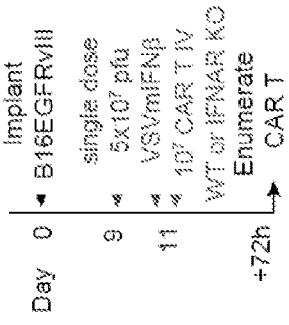

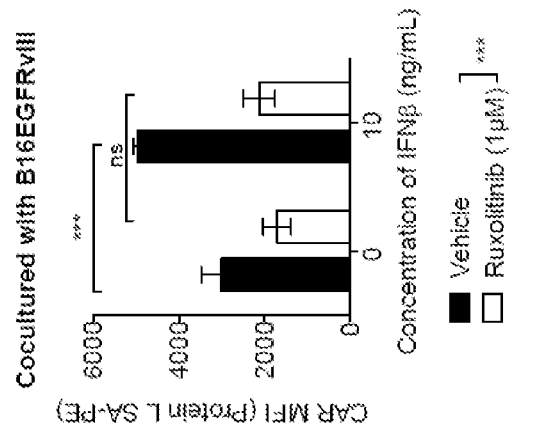
FIG. 3A  FIG. 3B
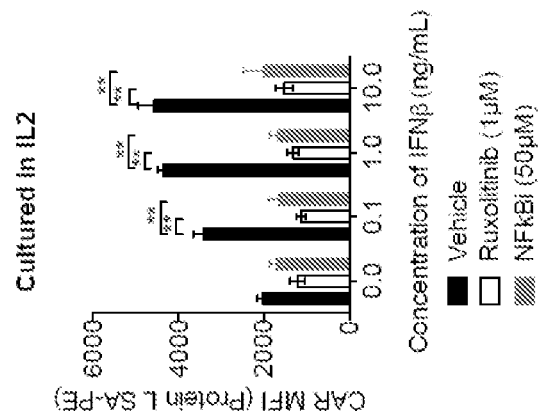
FIG. 3C  FIG. 3D
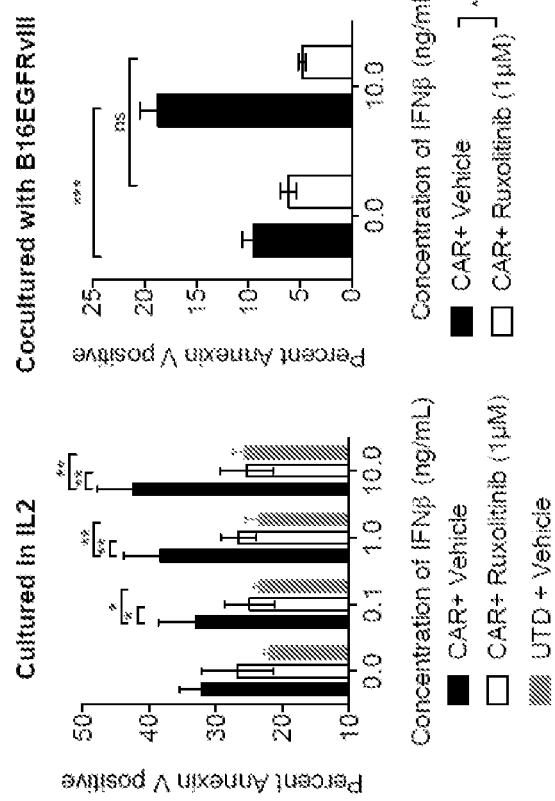

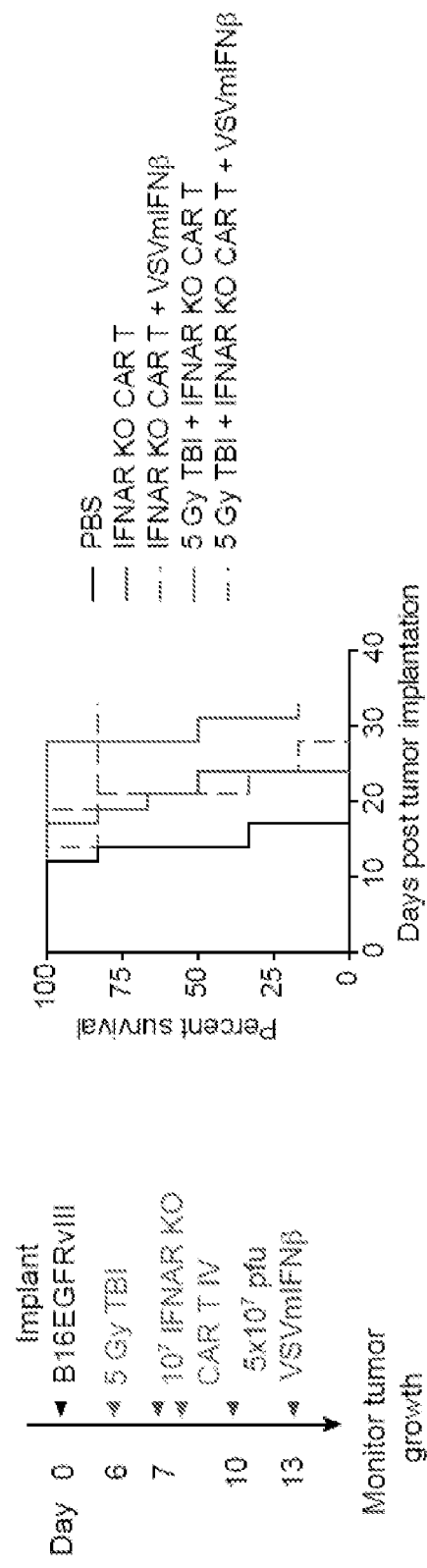
FIG. 4A
FIG. 4C
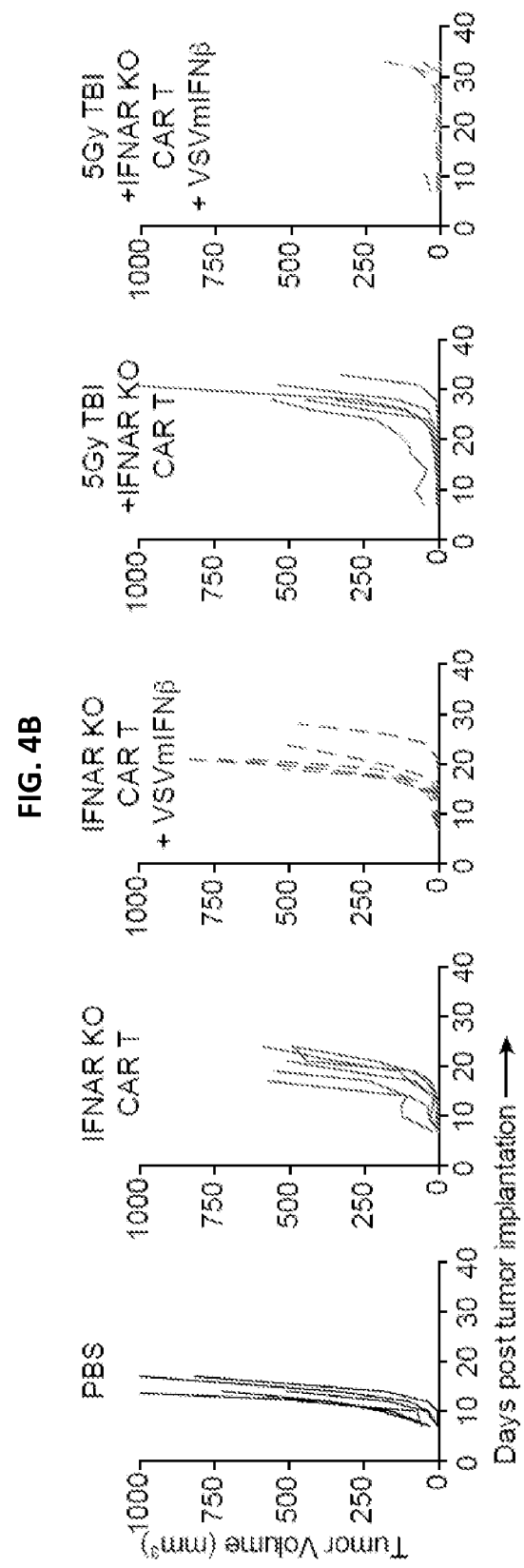
FIG. 4B

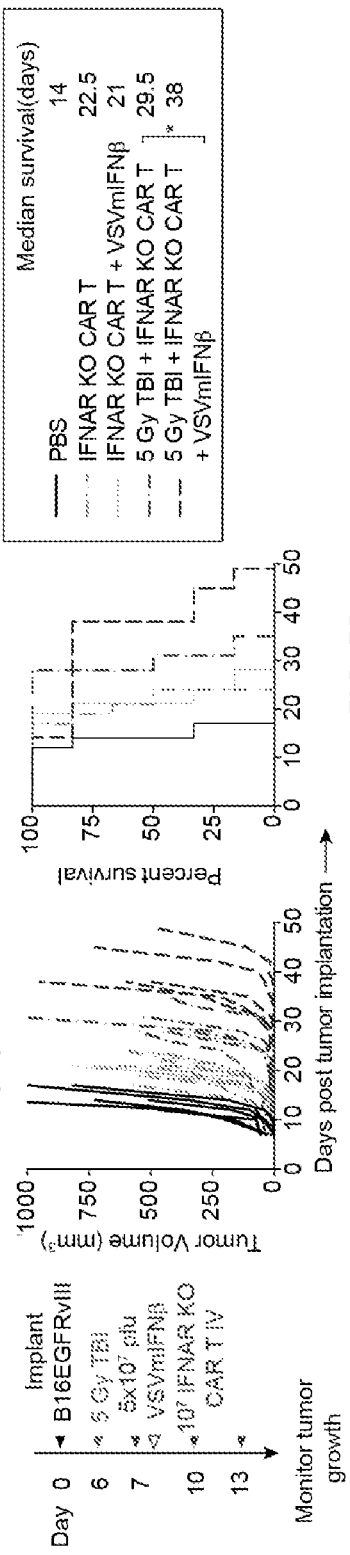
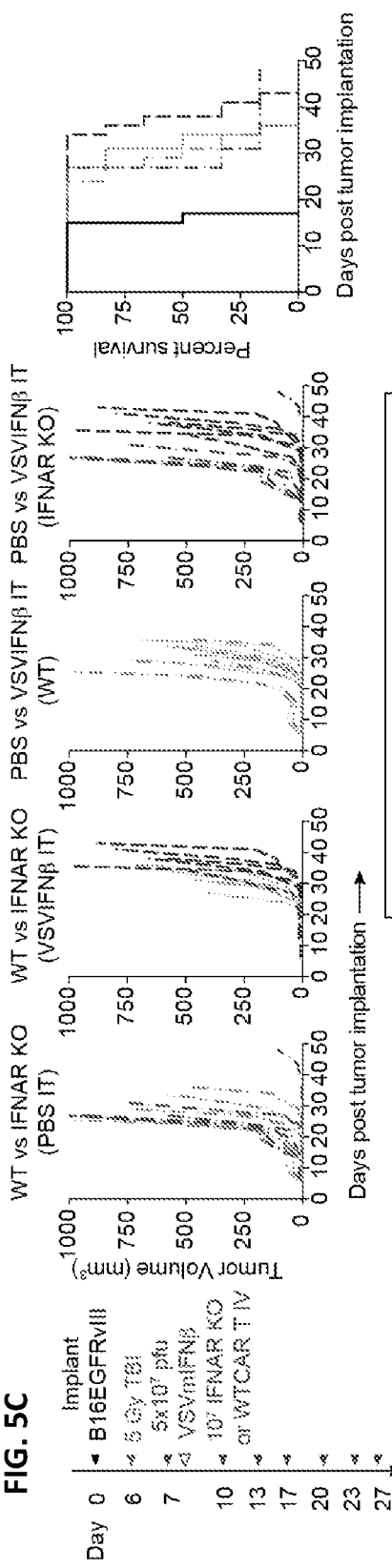

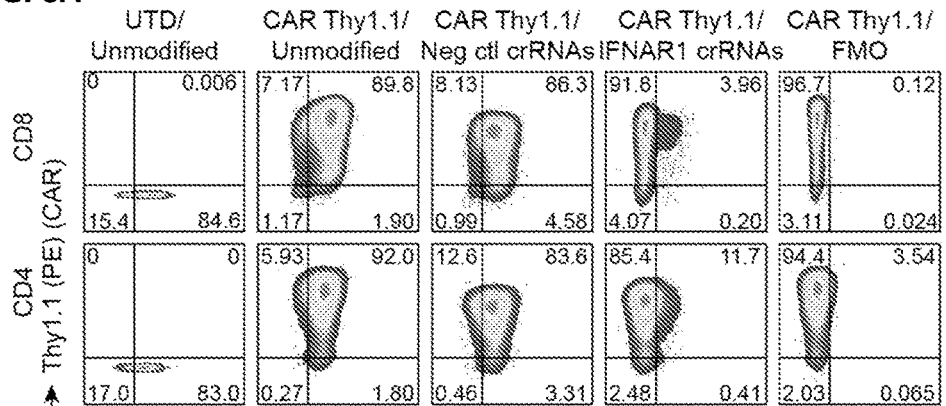
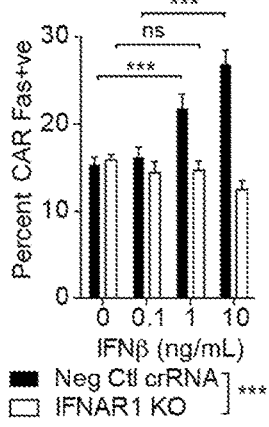
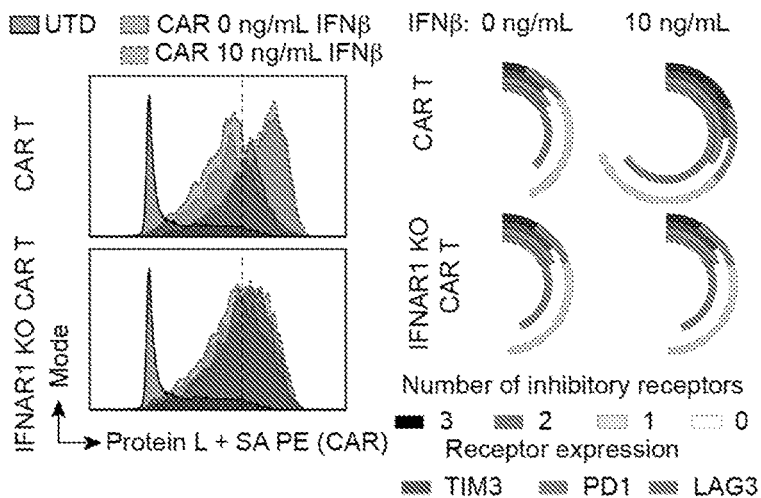
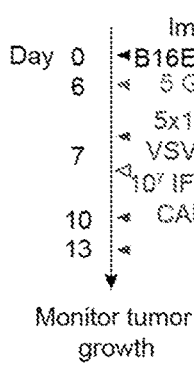
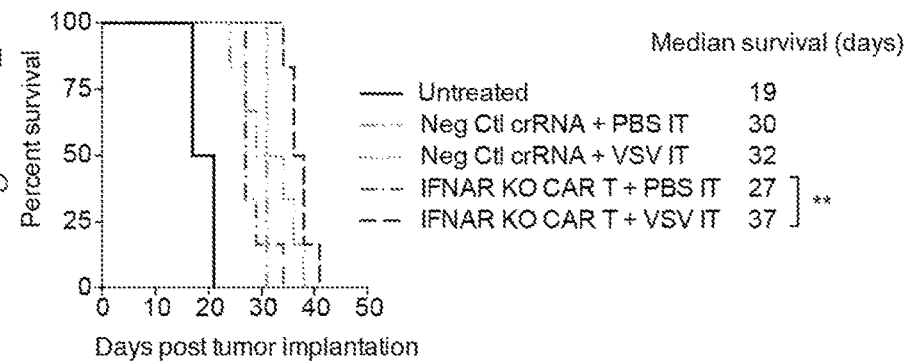

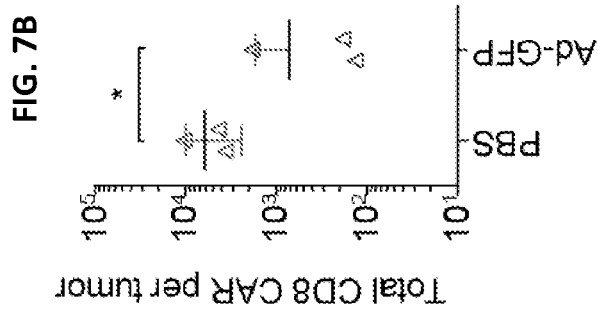
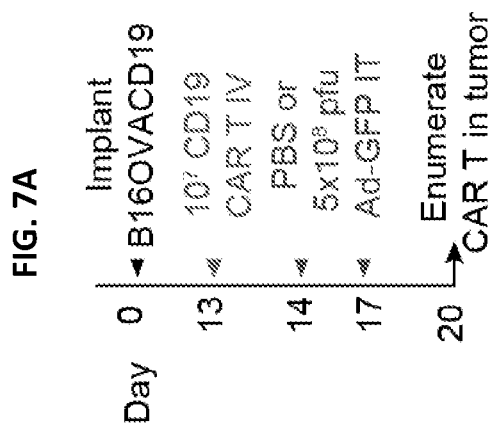
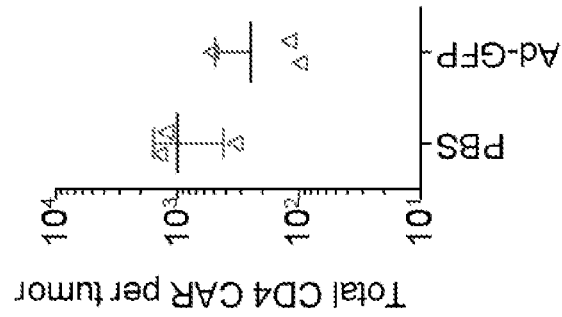

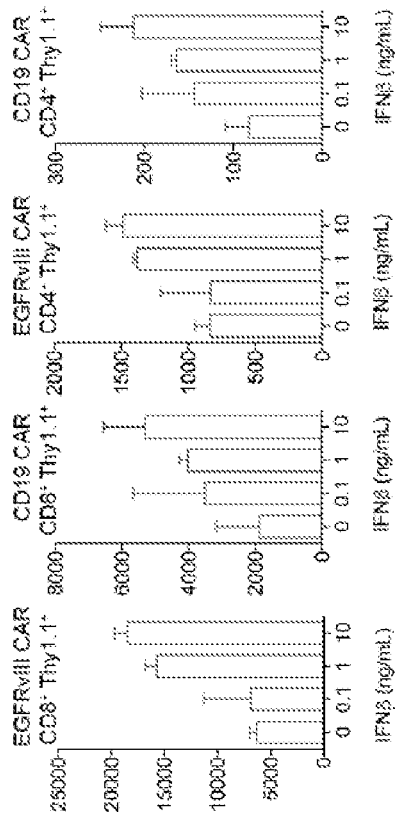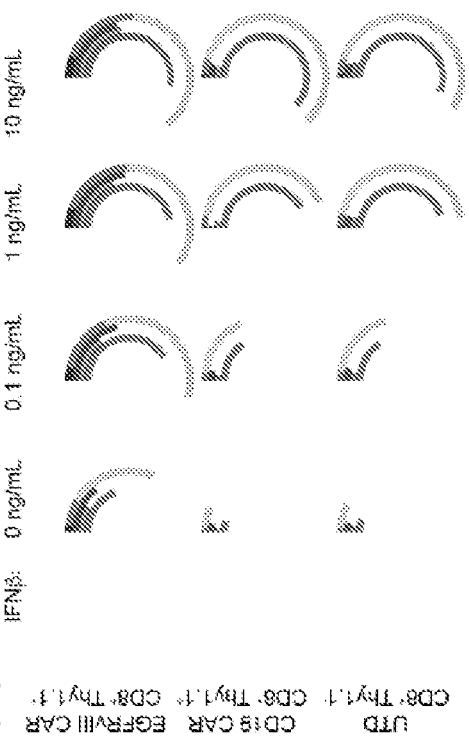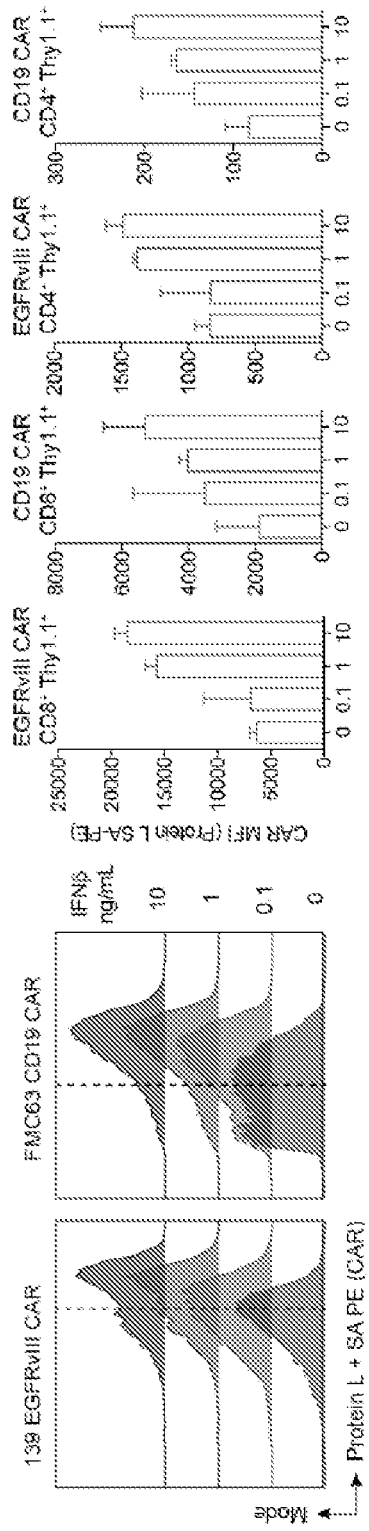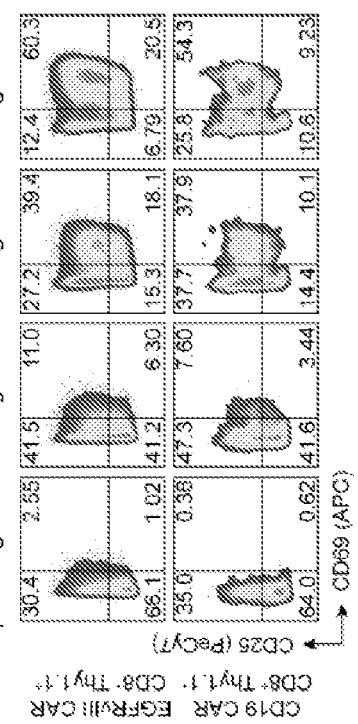
FIG. 8A
FIG. 8B
FIG. 8C
FIG. 8D

MATERIALS AND METHODS FOR TREATMENT WITH ONCOLYTIC VIRUSES AND MODIFIED CAR T CELLS

CROSS-REFERENCE TO RELATED APPLICATIONS

This application is a National Stage application under 35 U.S.C. § 371 of International Application No. PCT/US2019/050960, having an International Filing Date of Sep. 13, 2019, which claims priority to U.S. Application Ser. No. 62/731,560, filed on Sep. 14, 2018. The disclosure of the prior application is considered part of the disclosure of this application, and is incorporated in its entirety into this application.

TECHNICAL FIELD

This document relates to materials and methods for treating cancer. For example, this document provides materials and methods for using oncolytic viruses and genetically modified T cells that express a chimeric antigen receptor and do not express (or have reduced expression of) the type 1 interferon receptor.

BACKGROUND

Chimeric antigen receptor (CAR) modified T cells have been successfully used for treating hematologic malignancies, but multiple immune suppressive mechanisms limit their infiltration and drive their dysfunction in solid tumors. The insufficient migration of CAR T cells into the tumor reflects an unfavorable chemokine gradient for activated T cells that often is poor in CXCL9, 10, 11 and CCL5. Once CAR T cells do enter the tumor microenvironment (TME), interaction with suppressive immune populations such as regulatory T cells, MDSCs, and tumor associated macrophages can engage inhibitory ligands that promote exhaustion and/or apoptosis of T cells and also promote the secretion of inhibitory soluble mediators such as TGFβ, IL10, and adenosine, leading to suboptimal CAR T cell persistence and function.

Oncolytic viruses (OVs) are naturally selected to, or have been engineered to, replicate in cancer cells, but not in healthy cells. OVs initiate targeted infection and lysis of tumor beds and therefore can directly mediate debulking. OVs can be used to specifically express therapeutic transgenes in the tumor milieu. In addition, OV nucleic acids can activate Toll-like receptors (TLRs) and innate immune response pathways to initiate a pro-inflammatory cascade that stimulates the production of chemokines and cytokines, ultimately altering the balance of inhibitory and activating immune cells. The mechanism of tumor tropism of many oncolytic viruses, and Vesicular Stomatitis Virus (VSV) in particular, is predominantly mediated by the exquisite sensitivity of the virus to type I interferon (IFN), and the parallel loss of IFN responsiveness of tumor cells (Stojdl et al., Nat Med, 2000, 6(7):821-825). In order to increase the safety, specificity, and therapeutic index of VSV, IFNβ has been encoded between the glycoprotein and polymerase genes (Obuchi et al., J Virol, 2003, 77(16):8843-8856). Type I IFNs also can act as key signal 3 cytokines to facilitate the priming of tumor reactive T cells, and thus the therapeutic value of VSVIFNβ lies both in its ability to induce oncolysis and its ability to re-engage immune surveillance (Willmon et al., Cancer Res, 2009, 69(19):7713-7720). Critically, type I IFN binds to species-specific cell surface receptors with very limited cross-reactivity.

SUMMARY

This document is based on the discovery of an unexpected mechanism of antagonism in which VSVmIFNβ infection of a tumor induced profound attrition of CAR T cells. In studies described herein, the number of live CAR T cells was inversely proportional to the VSVmIFNβ titer and the type I IFN concentration in the tumor, and these two parameters were temporally synchronized. Further, type I IFN dysregulated CAR expression on the T cell surface, and sensitized the cells to exhaustion and apoptosis in a manner that was antigen independent. In contrast, interferon-α/β receptor knockout (IFNAR KO) CAR T cells were partially resistant to apoptosis induced by VSVmIFNβ in vivo, and importantly were able to provide additive therapy against B16EGFRvIII tumors in a combination therapy approach.

Thus, this document provides methods and materials for treating cancer. For example, this document provides methods and materials for treating cancer by administering (a) one or more OVs that induce expression of type I IFN, and (b) genetically modified T cells in which expression of the type I IFN receptor (e.g., interferon-α/β receptor (IFNAR)), or expression of another receptor that can signal T cell apoptosis or dysfunction upon expression of anti-viral innate factors following OV infection, has been disrupted.

In general, one aspect of this document features methods for treating a mammal having cancer. The methods can include (or consist essentially of or consist of) administering to the mammal an OV, where the OV induces expression of type I interferon (IFN), and administering to the mammal genetically modified T cells having reduced expression of IFNARs. The mammal can be a human. The OV is a rhabdovirus, reovirus, adenovirus, or herpes simplex virus. The rhabdovirus can be vesicular stomatitis virus or Maraba virus. The genetically modified T cells can express a chimeric antigen receptor, and the chimeric antigen receptor can be expressed from a retroviral vector or a lentiviral vector. The chimeric antigen receptor can target a tumor-associated antigen (e.g., CD19 or EGFRvIII). The genetically modified T cells can include a retrovirus or lentivirus expressing an shRNA targeted to a nucleic acid encoding the IFNAR (e.g., an IFNAR1 subunit or IFNAR2 subunit). The genetically modified T cells can include a genomic deletion of a nucleic acid encoding the IFNAR (e.g., an IFNAR1 subunit or IFNAR2 subunit). The OV and the genetically modified T cells can be administered to the mammal in an amount effective to kill tumor cells within the mammal. The OV and the genetically modified T cells can be administered in an amount effective to reduce metastasis of the tumor in the mammal. The cancer can be glioblastoma, pancreatic adenocarcinoma, cholangiocarcinoma, mesothelioma, melanoma, prostate cancer, breast cancer, ovarian cancer, liver cancer, colorectal cancer, or melanoma.

In another aspect, this document features a method for treating a mammal having cancer. The method comprises (or consists essentially of or consists of) administering, to the mammal, (a) a viral vector, wherein the viral vector induces expression of type I interferon (IFN) within the mammal, and (b) genetically modified T cells with reduced expression of interferon-α/β receptors (IFNARs). The mammal can be a human. The viral vector can be a rhabdovirus, reovirus, adenovirus, or herpes simplex virus. The viral vector can be a vesicular stomatitis virus or Maraba virus. The genetically modified T cells can express a chimeric antigen receptor. The chimeric antigen receptor can be expressed from a retroviral vector or a lentiviral vector. The chimeric antigen receptor can target a tumor-associated antigen. The tumor-associated antigen can be CD19 or EGFRvIII. The genetically modified T cells can comprise a retrovirus or lentivirus expressing an shRNA targeted to a nucleic acid encoding the IFNARs. The IFNARs can be IFNAR1 subunits or IFNAR2 subunits. The genetically modified T cells can comprise a genomic deletion of a nucleic acid encoding the IFNARs. The IFNARs can be IFNAR1 subunits or IFNAR2 subunits. The viral vector and the genetically modified T cells can be administered to the mammal in an amount effective to kill tumor cells within the mammal. The viral vector and the genetically modified T cells can be administered in an amount effective to reduce metastasis of the tumor in the mammal. The cancer can be selected from the group consisting of glioblastoma, pancreatic adenocarcinoma, cholangiocarcinoma, mesothelioma, melanoma, prostate cancer, breast cancer, ovarian cancer, liver cancer, colorectal cancer, and melanoma. The method can comprise administering a lymphodepleting regimen to the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1J are a series of graphs showing that oncolytic VSVmIFNβ infection has modest efficacy and promotes a favorable chemokine gradient for CAR T cell trafficking, but the combination does not improve survival over either modality. Mice bearing B16EGFRvIII tumors received a single intratumoral injection of $5 \times 10^7$ pfu of VSVmIFNβ or phosphate-buffered saline (PBS), and tumors were harvested 6, 24, or 48 hours post injection. Cytokine and chemokine concentrations (FIG. 1A) and infectious viral titer (FIG. 1B) were quantified in tumor homogenate lysates and normalized to the average tumor weight. N=3 per group except at the 48 hour time point, where N=2. FIG. 1C: Mice bearing B16EGFRvIII tumors were treated with $5 \times 10^7$ pfu VSVmIFNβ or PBS 6 hours prior to administration of $1 \times 10^7$ EGFRVIII CAR T cells on day 7. Select groups received two additional doses of $5 \times 10^7$ pfu VSVmIFNβ on days 10 and 13. N=6/group. Overall survival is shown in FIG. 1D, and tumor growth is shown in FIG. 1F. Circulating CD8 T CAR T cells were quantified from the blood 7 days after adoptive transfer (FIG. 1E). FIG. 1G: Mice bearing B16EGFRvIII tumors were given a lymphodepleting dose of radiation (5 Gy TBI) on day 6, and treated with $5 \times 10^7$ pfu VSVmIFNβ or PBS 6 hours prior to administration of $1 \times 10^7$ EGFRVIII CAR T cells on day 7. Select groups received two additional doses of $5 \times 10^7$ pfu VSVmIFNβ on days 10 and 13. Overall survival is shown in FIG. 1H and tumor growth is shown in FIG. 1J. Circulating CD8 T CAR T cells were quantified from the blood 6 days after adoptive transfer (FIG. 1I). ns, $P>0.05$: * $P \leq 0.05$: , $P \leq 0.01$: *, $P \leq 0.001$.

FIGS. 2A-2L are a series of graphs showing that oncolytic VSVmIFNβ infection promotes attrition of WT but not IFNAR KO CAR T cells in the tumor and spleen. FIG. 2A: Mice bearing B16EGFRvIII tumors received a single intratumoral injection of $5 \times 10^7$ pfu of VSVmIFNβ or PBS at various time points (6 to 72 hours) prior to adoptive transfer of $1 \times 10^7$ EGFRVIII CAR T cells on day 11. N=4/group. Three days post adoptive transfer, the number of viable CD8 (FIG. 2B) and CD4 (FIG. 2C) CAR T cells were quantified in the tumor: the number of viable CD8 (FIG. 2D) and CD4 (FIG. 2E) CAR T cells also were quantified in the spleen. FIG. 2F: Mice bearing B16EGFRvIII tumors received a single intratumoral injection of $5 \times 10^7$ pfu of VSVmIFNβ or VSVGFP or PBS 6 hours prior to adoptive transfer of $1 \times 10^7$ EGFRVIII CAR T cells on day 11. N=4/group. The next day, the number of viable CD8 CAR T cells was quantified in the tumor (FIG. 2G) and spleen (FIG. 2H). The concentration of IFNβ was additionally quantified in in tumor homogenate lysate and normalized by tumor weight (FIG. 2I). FIG. 2J: Mice bearing B16EGFRvIII tumors received a single intratumoral injection of $5 \times 10^7$ pfu of VSVmIFNβ or PBS 6 or 48 hours prior to adoptive transfer of $1 \times 10^7$ EGFRVIII CAR T cells prepared from WT C57Bl/6 mice or IFNAR KO mice. N=4/group. The number of viable CAR T cells was quantified in the tumor (FIG. 2K) and in the spleen (FIG. 2L). ns $P>0.05$: * $P \leq 0.05$:  $P \leq 0.01$: * $P \leq 0.001$.

FIGS. 3A-3H are a series of graphs showing that type I IFN promotes dysregulated expression of the CAR, exhaustion, and apoptosis. FIG. 3A: CAR T cells or untransduced (UTD) T cells were cultured in IL2 (50) U/mL) in the presence or absence of additional recombinant murine IFNβ and/or 1 µM Ruxolitinib (a Jak 1/2 inhibitor). The percent of AnnexinV positive CD8 CAR T cells is shown. FIG. 3B: CAR T cells or UTD T cells were cocultured with B16EGFRVIII cells at an E:T ratio of 1:5 in the presence or absence of additional recombinant murine IFNβ and/or 1 µM Ruxolitinib (Jak1/2 inhibitor). The percent of AnnexinV positive CD8 CAR T cells is shown. FIG. 3C: Cells were cultured as in FIG. 3A, with the addition of 50 µM Wedelolactone (NFKBi), and surface CAR expression on CD8 CAR T cells was quantified using Biotin-Protein L and streptavidin PE. FIG. 3D: Cells were cultured as in FIG. 3B, and surface CAR expression on CD8 CAR T cells was quantified using Biotin-Protein L and streptavidin PE. FIG. 3E: Exhaustion marker expression (PD1, Lag3, Tim3) quantified on CD8 CAR T or UTD cells cultured as in FIG. 3A. FIG. 3F: Cells were cultured as in FIG. 3B, and exhaustion marker expression (PD1, Lag3, Tim3) quantified on CD8 CAR T cells. FIG. 3G: CAR T cells prepared from WT C57Bl/6 mice or IFNAR KO mice were cocultured with B16EGFRVIII (E:T ratio of 1:5) that were mock infected or infected with VSVmIFNβ at an MOI of 0.01 or 0.1. Surface CAR expression on CD8 CAR T cells was quantified using Biotin-Protein L and streptavidin PE. (FIG. 3H: Exhaustion marker expression (PD1, Lag3, Tim3) quantified on WT or IFNAR KO CD8 CAR T cultured as in FIG. 3G. Means ±SD of technical triplicates are shown. ns, $P>0.05$: *, $P \leq 0.05$: , $P \leq 0.01$; and *, $P \leq 0.001$.

FIGS. 4A-4C are a series of graphs showing that type I IFN resistant CAR T cells provide additive therapy with VSVmIFNβ in lymphodepleted mice. FIG. 4A: Mice bearing B16EGFRvIII tumors were treated with $5 \times 10^7$ pfu VSVmIFNβ or PBS 6 hours prior to administration of $1 \times 10^7$ IFNAR KO EGFRVIII CAR T cells on day 7. Select groups received two additional doses of $5\times10^7$ pfu VSVmIFNβ on days 10 and 13. Select groups received a lymphodepleting dose of radiation (5 Gy TBI) on day 6. N=6/group. Tumor growth is plotted in FIG. 4B, and overall survival is plotted in FIG. 4C.

FIGS. 5A-5D are a series of graphs showing that type I IFN resistant CAR T cells provide additive therapy with VSVmIFNβ in lymphodepleted mice. FIG. 5A: Mice bearing B16EGFRvIII tumors were treated with $5\times10^7$ pfu VSVmIFNβ or PBS 6 hours prior to administration of $1\times10^7$ transgenic IFNAR1 KO EGFRVIII CAR T cells on day 7. Select groups received 2 additional doses of $5\times10^7$ pfu VSVmIFNβ. Select groups received a lymphodepleting dose of radiation (5 Gy TBI) on day 6. N=6/group. FIG. 5B: Tumor growth is shown in the left panel and overall survival is shown in right panel. FIG. 5C: Mice bearing B16EGFRvIII tumors were lymphodepleted on day 6 and treated with $5\times10^7$ pfu VSVmIFNβ or PBS 6 hours prior to administration of $1\times10^7$ transgenic IFNAR1 KO or WT EGFRVIII CAR T cells on day 7. Select groups received 6 additional doses of $5\times10^7$ pfu VSVmIFNβ. N=6/group. FIG. 5D: Tumor growth for relevant comparisons are overlaid in the middle panel, and overall survival is shown in right panel. P-values were determined using the Log-rank Mantel-Cox test (FIGS. 5B and 5D) ns $P>0.05$: * $P\leq0.05$; and ** $P\leq0.01$.

FIGS. 6A-6F are a series of graphs showing that CRISPR disruption of IFNAR1 expression in CAR T cells renders cells insensitive to IFNβ and improves tumor control in combination with VSVmIFNβ. FIG. 6A: CAR T cells were genetically modified using CRISPR Cas9 by nucleofection of RNP complexes containing two IFNAR1 specific or two negative control crRNAs duplexed with tracrRNA and Cas9. Expression of the CAR (Thy 1.1) and the IFNAR1 is shown (48 hours post modification). FIG. 6B: CRISPR modified CAR T cells were cultured in IL-2 (50 U/mL) in the absence or presence of additional recombinant mouse IFNβ. Mean Fas expression was quantified. FIG. 6C: CAR expression is shown for representative CD8 CAR T cells in the absence or presence of additional recombinant mouse IFNβ. FIG. 6D: Mean inhibitory receptor expression of PDI, LAG3, and TIM3 was quantified on CRISPR IFNAR1 KO or control CD8 CAR T cells cultured in the absence or presence of additional recombinant mouse IFNβ. FIG. 6E: Mice bearing B16EGFRvIII tumors were lymphodepleted on day 6 and treated with $5\times10^7$ pfu VSVmIFNβ or PBS 6 hours prior to administration of $1\times10^7$ CRISPR modified IFNAR1 KO or negative control crRNA EGFRVIII CAR T cells on day 7. Select groups received two additional doses of $5\times10^7$ pfu VSVmIFNβ. Overall survival is shown in FIG. 6F. P-values were determined using the Log-rank Mantel-Cox test (FIG. 6F) and a two-way ANOVA with a Tukey post-test (FIG. 6B). Means+SD of technical triplicates are shown. ns $P>0.05$:  $P\leq0.01$; and * $P\leq0.001$.

FIGS. 7A-7B are a series of graphs showing that another viral vector is associated with CAR T cell attrition. Mice bearing subcutaneous B16OVA-CD19 tumors were treated with $10^7$ CD19 specific CAR T cells on day 7 post implantation and two doses of intratumoral (IT) phosphate buffered saline (PBS) or $5\times10^8$ pfu of replication defective Adenovirus expressing GFP on days 14 and 17. CAR T cells in the tumor were enumerated on day 20. N=3 mice/group. P-values were determined using a T test. * $P\leq0.05$.

FIGS. 8A-8D. CD19 CAR T cells treated with IFNβ in vitro. EGFRvIII-specific CAR T cells (with the scFv 139) and CD19-specific CAR T cells (with the scFv FMC63) were cultured in IL2 in the absence or presence of recombinant murine IFNβ, and CAR expression on the surface was measured using Biotin-Protein L and recognized with streptavidin-PE (Protein L+SA PE). Representative staining is shown in FIG. 8A, and the mean of three technical replicates was quantified in FIG. 8B. FIG. 8C: Representative expression of the activation markers CD25 and CD69 were shown for CAR T cells cultured as in FIG. 8A. FIG. 8D: Inhibitory receptor expression (PD1, LAG3, and TIM3) was quantified on CD8 CAR T or UTD cells cultured as in FIG. 8A. Average expression of three technical replicates is shown.

DETAILED DESCRIPTION

Figure 2E:
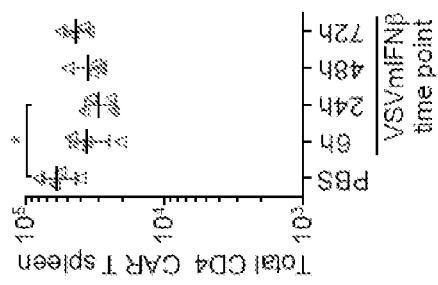
Figure 2D:
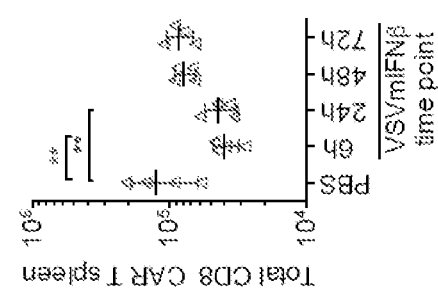
Figure 2C:
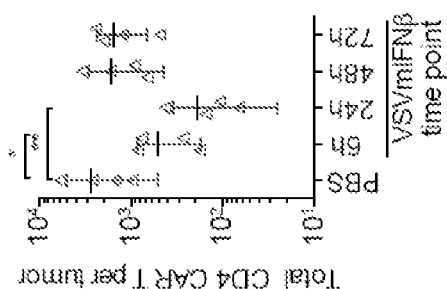
Figure 2B:
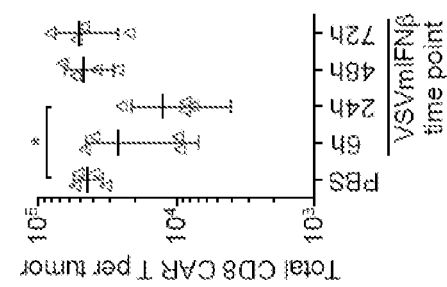

This document provides methods and materials for treating cancer. For example, one or more OVs can be administered to a mammal (e.g., a mammal having, or at risk of having, cancer) in combination with an adoptive cell therapy (e.g., a CAR T cell therapy using genetically modified CAR T cells as described herein), in order to reduce the number of cancer cells (e.g., by infecting and killing cancer cells) in the mammal.

Any appropriate mammal having, or at risk of having, cancer can be treated as described herein. For example, humans, non-human primates, monkeys, horses, bovine species, porcine species, dogs, cats, mice, and rats having cancer can be treated for cancer as described herein. In some cases, a human having cancer can be treated. In some cases, a mammal (e.g., a human) treated as described herein is not a natural host of an OV used in the methods provided herein. For example, a human being treated with an OV described herein can lack any pre-existing adaptive immunity to the OV.

A mammal having any appropriate type of cancer can be treated as described herein (e.g., treated with (a) one or more OVs and (b) an adoptive cell therapy, such as genetically modified CAR T cells as described herein). In some cases, a cancer treated as described herein can include one or more solid tumors. In some cases, a cancer treated as described herein can be a blood cancer. In some cases, a cancer treated as described herein can be a primary cancer. In some cases, a cancer treated as described herein can be a metastatic cancer. In some cases, a cancer treated as described herein can be a refractory cancer. In some cases, a cancer treated as described herein can express a tumor-associated antigen (e.g., an antigenic substance produced by a cancer cell). Examples of cancers that can be treated as described herein include, without limitation, brain cancers (e.g., glioblastoma), pancreatic cancers (e.g., pancreatic adenocarcinoma), bile duct cancers (e.g., cholangiocarcinoma), lung cancers (e.g., mesothelioma), skin cancers (e.g., melanoma), prostate cancers, breast cancers, ovarian cancers, liver cancers, colorectal cancers, germ cell tumors, hepatocellular carcinoma, bowel cancers, multiple myeloma, lymphomas (e.g., B cell lymphomas such as diffuse large cell lymphoma), and leukemias (e.g., chronic lymphocytic leukemia (CLL), acute lymphoblastic leukemia (ALL), and acute myeloid leukemia (AML)). In some cases, a cancer treated as described herein can be a glioblastoma. In some cases, a cancer treated as described herein can be a pancreatic adenocarcinoma. In some cases, a cancer treated as described herein can be an ovarian cancer. For example, a cancer treated as described herein can be a melanoma.

Any suitable OV can be used in the methods provided herein. Suitable OVs include, without limitation, Rhabdoviruses (e.g., Vesicular stomatitis virus or Maraba virus), Reovirus, Adenovirus, vaccinia viruses, or herpes simplex virus.

In some cases, an OV used in the methods described herein can be replication competent or can be replication defective.

In some cases, an OV can be non-pathogenic (e.g., to a mammal being treated as described herein). For example, an OV can be genetically modified to render it non-pathogenic to a mammal to be treated.

In some cases, an OV can infect dividing cells (e.g., can infect only dividing cells).

In some cases, an OV can bud through the endoplasmic reticulum.

In some cases, an OV can bind to a cellular receptor (e.g., to facilitate viral entry to a cell).

Nucleic acids that can be included in an OV genome include, for example, gag nucleic acid (e.g., nucleic acid encoding the group-specific antigen protein), pol nucleic acid (e.g., nucleic acid encoding the DNA polymerase), and env nucleic acid (e.g., nucleic acid encoding the envelope protein). Viral elements that can be included in an OV genome include, without limitation, a 5' long terminal repeat (LTR) and a 3' LTR, each of which can include a U3 region, a R region, and a U5 region.

One or more OVs can be used in combination with an adoptive T cell therapy (e.g., a CAR T cell therapy) targeting any appropriate antigen within a mammal (e.g., a mammal having cancer). In some cases, an antigen can be a tumor-associated antigen (e.g., an antigenic substance produced by a cancer cell). Examples of tumor associated antigens that can be targeted by an adoptive T cell therapy provided herein include, without limitation, cluster of differentiation 19 (CD19; associated with B cell lymphomas, acute lymphoblastic leukemia (ALL), and chronic lymphocytic leukemia (CLL)), alphafetoprotein (AFP: associated with germ cell tumors and/or hepatocellular carcinoma), carcinoembryonic antigen (CEA: associated with bowel cancer, lung cancer, and/or breast cancer), CA-125 (associated with ovarian cancer), mucin 1 (MUC-1: associated with breast cancer), epithelial tumor antigen (ETA: associated with breast cancer), melanoma-associated antigen (MAGE: associated with malignant melanoma), CD33 (associated with AML), CD123 (associated with AML), CLLI (associated with AML), HER2 (associated with breast or ovarian cancer), EGFR (associated with lung, ovarian, or colon cancer), EGFRviii (associated with brain cancer), IL13R (associated with brain cancer), EPhA3 (associated with brain cancer), BCMA (associated with myeloma), CSI (associated with myeloma), CD38 (associated with myeloma), CD138 (associated with myeloma or AML), FAP (associated with different cancers), CALR (associated with myeloid cancer), Mesothelin (associated with mesothelioma or pancreatic cancer), MUC (associated with breast cancer), CD22 (associated with B cell malignancies), Kappa (associated with B cell malignancies), Lambda (associated with B cell malignancies), CD20) (associated with B cell malignancies), CD30 (associated with Hodgkin lymphoma), CD3 (associated with T cell leukemia/lymphoma) CD5 (associated with T cell leukemia/lymphoma), CD7 (associated with T cell leukemia/lymphoma), and CD2 (associated with T cell leukemia/lymphoma). For example, one or more OVs can be used in combination with CART cell therapy targeting CD19 (e.g., CART19 cell therapy) to treat cancer as described herein.

The genetically modified CAR T cells used in the methods provided herein can have reduced expression of any appropriate receptor that signals T cell apoptosis or dysfunction upon expression of anti-viral innate factors following OV infection (e.g., an IFNAR such as IFNAR1 or IFNAR2). In some cases, a genetically modified CAR T cell can have a reduced level of IFNARs. The term "reduced level" as used herein with respect to an expression level of IFNAR (or another suitable receptor) refers to any level that is lower than a reference expression level of IFNAR (or another suitable receptor). The term "reference level" as used herein with respect to IFNAR (or another suitable receptor) refers to the level of IFNAR (or another suitable receptor) typically observed in a sample (e.g., a control sample) from one or more mammals (e.g., humans) not engineered to have a reduced expression level of that receptor. Control samples can include, without limitation, T cells that are wild-type T cells (e.g., T cells that are not IFNAR KO T cells). In some cases, a reduced expression level of a receptor can be an undetectable level of that receptor. In some cases, a reduced expression level of IFNAR (or another suitable receptor) can be an eliminated level of that receptor.

In some cases, a T cell having (e.g., engineered to have) a reduced expression level of IFNAR (or another suitable receptor) such as an IFNAR KO CAR T cell can maintain normal T cell functions such as T cell degranulation and release of cytokines (e.g., as compared to a CART that is not engineered to have a reduced expression level of IFNAR (or another suitable receptor) as described herein).

In some cases, a T cell having (e.g., engineered to have) a reduced level of IFNAR (or another suitable receptor) such as an IFNAR CAR T cell can have enhanced CART function such as antitumor activity (e.g., as compared to a CART that is not engineered to have a reduced level of IFNAR (or another suitable receptor) as described herein).

In some cases, a T cell having (e.g., engineered to have) a reduced level of IFNAR (or another suitable receptor) such as an IFNAR CAR KO T cell can have enhanced T cell expansion (e.g., as compared to a CART that is not engineered to have a reduced level of IFNAR (or another suitable receptor) as described herein).

A T cell having (e.g., engineered to have) a reduced expression level of IFNAR (or another suitable receptor) such as an IFNAR CAR KO T cell can be any appropriate T cell. A T cell can be a naïve T cell. Examples of T cells that can be designed to have a reduced expression level of IFNAR (or another suitable receptor) as described herein include, without limitation, cytotoxic T cells (e.g., CD4+ CTLs and/or CD8+CTLs). For example, a T cell that can be engineered to have a reduced level of IFNAR (or another suitable receptor) as described herein can be a CART. In some cases, one or more T cells can be obtained from a mammal (e.g., a mammal having cancer). For example, T cells can be obtained from a mammal to be treated with the materials and method described herein.

A T cell having (e.g., engineered to have) a reduced expression level of IFNAR (or another suitable receptor) such as an IFNAR CAR KO T cell can be generated using any appropriate method. In some cases, a T cell (e.g., CART) can be engineered to KO a nucleic acid encoding an IFNAR (or another suitable receptor) to reduce IFNAR (or another suitable receptor) polypeptide expression in that T cell. In cases where a T cell (e.g., CART is engineered to KO a nucleic acid encoding an IFNAR), any appropriate IFNAR subunit (e.g., IFNAR1 or IFNAR2) can be targeted.

In some cases, when a T cell (e.g., CART) is engineered to KO a nucleic acid encoding an IFNAR (or another suitable receptor) to reduce expression of an IFNAR (or another suitable receptor) polypeptide in that T cell, any appropriate method can be used to KO a nucleic acid encoding IFNAR (or another suitable receptor). Examples of techniques that can be used to knock out a nucleic acid sequence encoding IFNAR (or another suitable receptor) include, without limitation, gene editing and homologous recombination. For example, gene editing (e.g., with engineered nucleases) can be used to KO a nucleic acid encoding an IFNAR (or another suitable receptor) polypeptide. Nucleases useful for genome editing include, without limitation, CRISPR-associated (Cas) nucleases, zinc finger nucleases (ZFNs), transcription activator-like effector (TALE) nucleases, and homing endonucleases (HE: also referred to as meganucleases).

A CRISPR/Cas system used to KO a nucleic acid encoding an IFNAR (or another suitable receptor) polypeptide can include any appropriate Cas nuclease. Examples of Cas nucleases include, without limitation, Cas1, Cas2, Cas3, Cas9, Cas10, and Cpf1. In some cases, a Cas component of a CRISPR/Cas system designed to KO a nucleic acid encoding an IFNAR (or another suitable receptor) polypeptide can be a Cas9) nuclease.

In some cases, a T cell (e.g., a CART) can be treated with one or more inhibitors of IFNAR (or another suitable receptor) polypeptide expression or IFNAR (or another suitable receptor) polypeptide activity to reduce IFNAR (or another suitable receptor) polypeptide expression in that T cell (e.g., as compared to a T cell that was not treated with one or more inhibitors of IFNAR (or another suitable receptor) polypeptide expression or IFNAR (or another suitable receptor) polypeptide activity). An inhibitor of IFNAR (or another suitable receptor) polypeptide expression or IFNAR (or another suitable receptor) polypeptide activity can be any appropriate inhibitor. Example of inhibitors of IFNAR (or another suitable receptor) polypeptide expression or IFNAR (or another suitable receptor) polypeptide activity include, without limitation, nucleic acid molecules designed to induce RNA interference (e.g., a siRNA molecule or a shRNA molecule), antisense molecules, miRNAs, and antibodies (e.g., antagonistic antibodies). In some cases, an inhibitor of an IFNAR (or another suitable receptor) can be a shRNA molecule. For example, a T cell can include viral vector (e.g., a retroviral vector or a lentiviral vector) expressing a shRNA targeted to a nucleic acid encoding the IFNAR (e.g., (e.g., an IFNAR1 subunit or an IFNAR2 subunit).

A T cell having (e.g., engineered to have) a reduced expression level of IFNAR (or another suitable receptor) can express (e.g., can be engineered to express) any appropriate antigen receptor. In some cases, an antigen receptor can be a heterologous antigen receptor. In some cases, an antigen receptor can be a CAR. In some cases, an antigen receptor can be a tumor antigen (e.g., tumor-specific antigen) receptor. For example, a T cell can be engineered to express a tumor-specific antigen receptor that targets a tumor-specific antigen (e.g., a cell surface tumor-specific antigen) expressed by a cancer cell in a mammal having cancer. Examples of antigens that can be recognized by an antigen receptor expressed in a T cell having reduced expression of a IFNAR (or another suitable receptor) as described herein include, without limitation, cluster of differentiation 19 (CD19), mucin 1 (MUC-1), human epidermal growth factor receptor 2 (HER-2), estrogen receptor (ER), epidermal growth factor receptor (EGFR), alphafetoprotein (AFP), carcinoembryonic antigen (CEA), CA-125, epithelial tumor antigen (ETA), and melanoma-associated antigen (MAGE). For example, a T cell having a reduced level of IFNARs (or another suitable receptors) can be designed to express an antigen receptor targeting CD19.

Any appropriate method can be used to express an antigen receptor on a T cell having (e.g., engineered to have) a reduced expression level of IFNAR (or another suitable receptor). For example, a nucleic acid encoding an antigen receptor can be introduced into one or more T cells. In some cases, viral transduction can be used to introduce a nucleic acid encoding an antigen receptor into a non-dividing a cell. A nucleic acid encoding an antigen receptor can be introduced in a T cell using any appropriate method. In some cases, a nucleic acid encoding an antigen receptor can be introduced into a T cell by transduction (e.g., viral transduction using a viral vector such as a retroviral vector or a lentiviral vector) or transfection (e.g., transfection by electroporation). In some cases, a nucleic acid encoding an antigen receptor can be introduced ex vivo into one or more T cells. For example, ex vivo engineering of T cells expressing an antigen receptor can include transducing isolated T cells with a viral vector encoding an antigen receptor. In cases where T cells are engineered ex vivo to express an antigen receptor, the T cells can be obtained from any appropriate source (e.g., a mammal such as the mammal to be treated or a donor mammal, or a cell line).

The OVs and genetically modified CAR T cells used in the methods described herein can be formulated into compositions (e.g., pharmaceutical compositions) for administration to a mammal (e.g., a mammal having, or at risk of having, cancer). For example, one or more OVs and/or genetically modified CAR T cells can be formulated into a pharmaceutically acceptable composition for administration to a mammal having, or at risk of having, cancer. In some cases, the one or more OVs and/or genetically modified CAR T cells can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A composition containing one or more OVs and can be combined with materials for use in an adoptive T cell therapy (e.g., CAR T cell therapy) and with packaging material, and configured into a kit. The packaging material included in a kit can contain instructions or a label describing how the composition can be used, for example, in combination with an adoptive cell therapy (e.g., CART cell therapy) to treat a mammal having cancer.

This document also provides methods for using OVs and genetically modified CAR T cells described herein. In some cases, one or more OVs and a population of genetically modified CAR T cells can be used for treating a mammal having, or at risk of having, cancer. For example, methods for treating a mammal having, or at risk of having, cancer can include administering (a) one or more OVs and (b) genetically modified CAR T cells described herein to the mammal. In some cases, methods for treating a mammal having, or at risk of having, cancer can include administering one or more expression vectors or nucleic acids that encode an OV described herein to the mammal, in combination with genetically modified CAR T cells. In some cases, the OVs and genetically modified CAR T cells described herein can be administered to a mammal to reduce the number of cancer cells in the mammal (e.g., to suppress and/or delay tumor growth) and/or to increase survival of the mammal. For example, one or more OVs and genetically modified CAR T cells described herein can be administered to a mammal to induce cell death in a cell of the mammal (e.g., in an infected cell of the mammal).

In some cases, methods described herein also can include identifying a mammal as having cancer. Examples of methods for identifying a mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, a mammal can be administered or instructed to self-administer one or more OVs (or a nucleic acid or expression vector encoding one or more OVs) and genetically modified CAR T cells described herein.

One or more OVs and genetically modified CAR T cells as described herein can be administered to a mammal by any appropriate route (e.g., intravenous, intramuscular, subcutaneous, oral, intranasal, inhalation, transdermal, or parenteral). In some cases, one or more OVs and genetically modified T cells described herein can be administered intravenously to a mammal (e.g., a human). In some cases, a composition (e.g., a pharmaceutical composition) containing one or more OVs used in combination with an adoptive T cell therapy (e.g., a CART cell therapy) can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

A composition (e.g., a pharmaceutical composition) containing one or more OVs used in combination with an adoptive T cell therapy (e.g., a CART cell therapy) can be administered locally or systemically. For example, a composition containing one or more OVs can be administered systemically by oral administration or by injection to a mammal (e.g., a human).

One or more OVs used in combination with an adoptive T cell therapy (e.g., a CART cell therapy) can be administered in any appropriate order with respect to the administration of the adoptive T cell therapy. In some cases, a composition including one or more OVs can be administered concurrently with administration of the adoptive T cell therapy. For example, a composition including one or more OVs can be administered to the mammal at any time during the course of an adoptive T cell therapy procedure. In some cases, a composition including one or more OVs can be administered in series with administration of the adoptive T cell therapy. For example, a composition including one or more OVs can be administered before, after, or both before and after the adoptive T cell therapy procedure. In some cases, a composition including one or more OVs can be administered before, during, and after the adoptive T cell therapy procedure.

Effective doses of one or more OVs and adoptive T cell therapies can vary depending on the severity of the cancer, the route of administration, the age and general health of the subject, excipient usage, the possibility of co-usage with other therapeutic treatments such as the use of other agents, and the judgment of the treating physician.

One or more OVs and an adoptive T cell therapy as described herein can be administered to a mammal in an amount effective to reduce the number of tumor cells in the mammal, to kill tumor cells in the mammal, to increase survival of the mammal, to reduce or prevent metastasis of the tumor in the mammal, and/or to reduce one or more symptoms of cancer in the mammal, without producing significant toxicity to the mammal. For example, an OV and an adoptive T cell therapy can be administered in an amount effective to reduce the number of tumor cells in the mammal by at least about 5% (e.g., 10%, 20%, 25%, 30%, 50%, or more than 50%) as compared to the number of tumor cells in the mammal before treatment. In some cases, an OV and an adoptive T cell therapy can be administered in an amount effective to prolong survival (e.g., overall survival or progression-free survival) of the mammal by at least about 5% (e.g., 10%, 20%, 25%, 30%, 50%, or more than 50%) as compared to a corresponding untreated mammal having the same time of cancer, for example. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., a cancer) may require an increase or decrease in the actual effective amount administered.

The frequency of administration of a combination therapy that includes one or more OVs and an adoptive T cell therapy can be any frequency that alters (e.g., enhances or suppresses) one or more functions of a CART cell and/or enhances CART cell expansion without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with one or more OVs and genetically modified CAR T cells described herein can include rest periods. For example, one or more OVs and genetically modified CAR T cells described herein can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., a cancer) may require an increase or decrease in administration frequency.

In some cases, the number of cancer cells present within a mammal, and/or the severity of one or more symptoms related to the cancer being treated can be monitored. Any appropriate method can be used to determine whether or not the number of cancer cells present within a mammal is reduced. For example, imaging techniques can be used to assess the number of cancer cells present within a mammal.

In some cases, methods described herein also can include administering to a mammal (e.g., a mammal having cancer) one or more additional agents used to treat a cancer. The one or more additional agents used to treat a cancer can include any appropriate cancer treatment. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. For example, a mammal having cancer can be administered one or more OVs and genetically modified CAR T cells described herein, and also administered one or more additional agents used to treat a cancer. The one or more additional agents used to treat a cancer can be administered to the mammal at the same time as or independently from the one or more OVs and genetically modified CAR T cells. For example, one or more OVs described herein and one or more additional agents used to treat a cancer can be formulated together to form a single composition, and administered with a composition containing genetically modified CAR T cells. For example, genetically modified CAR T cells and one or more additional agents used to treat a cancer can be formulated together to form a single composition, and administered with a composition containing one or more OVs. For example, one or more OVs, genetically modified CAR T cells, and one or more additional agents used to treat a cancer can be formulated together to form a single composition. In some cases, one or more OVs and genetically modified CAR T cells described herein can be administered first, and the one or more additional agents used to treat a cancer administered second, or vice versa.

In some cases, one or more OVs and genetically modified CAR T cells described herein can be administered in combination with a lymphodepleting regimen. Examples of lymphodepletion regimens include, without limitation, treatment with cyclophosphamide, treatment with fludarabine, and treatment with radiation (e.g., whole body radiation).

In some cases, the one or more OVs of a method or composition described herein can be replaced with a viral vector that is not oncolytic. For example, non-oncolytic viral vectors can be used in combination with genetically modified CAR T cells described herein to treat cancer. Examples of non-oncolytic viral vectors that can be used in place of the OVs for a method or composition described herein include, without limitation, replication defective, non-oncolytic adenoviral vectors, non-oncolytic AAV viral vectors, and non-oncolytic retroviral viral vectors.

The invention will be further described in the following examples, which do not limit the scope of the invention described in the claims.

EXAMPLES

Example 1—Oncolytic VSVmIFNβ Infection has Modest Efficacy and Promotes a Favorable Chemokine Gradient for CAR T Cell Trafficking, but the Combination does not Improve Survival Over Either Modality A B16 subcutaneous model that overexpressed the CAR target antigen EGFRVIII was established and used to evaluate how VSVmIFNβ infection alters the cytokine and chemokine profile of the tumor microenvironment. A single intratumoral injection induced high level expression of the transgene IFNβ that peaked between 6 and 24 hours post infection (hpi) and that that was sustained out to 48 hpi (FIG. 1A). IFNβ was also induced along with a variety of inflammatory chemokines including CCL5, CXCL01, CCL2 and CXCL1, and their expression mirrored the kinetics of viral replication in the tumor (FIGS. 1A and 1B). Given the rapid induction of chemokines in the infected tumors that might recruit CXCR3+ and CCR5+CAR T cells, VSVmIFNβ was administered 6 hours prior to adoptive transfer of third generation murine EGFRVIII CAR T cells to determine whether OV priming of the tumor could potentiate antitumor CAR T cell therapy (FIG. 1C). Although a very modest reduction in tumor growth rate was observed with each modality, a significant therapeutic benefit to the combination of VSVmIFNβ and EGFRVIII CAR T cells was not observed (FIGS. 1D and 1F). Submandibular bleeds were performed 7 days post adoptive transfer to quantify circulating CAR T cells, revealing a surprising 3-fold reduction in the number of CD8 CAR T cells (FIG. 1E).

The same schedule of VSVmIFNβ and EGFRVIII CAR T cell mono- or combination therapy was repeated in mice that received a lymphodepleting dose of whole body irradiation to fully capture the therapeutic potential of the CAR T cells (FIG. 1G). Although the magnitude of the therapeutic effect of each modality was improved relative to non-preconditioned mice, no improvement in overall survival or tumor control was observed with the combination approach (FIGS. 1H and 1J). Similarly, CD8 CAR T cell attrition was observed in the blood of mice that received a single dose or three doses of VSVmIFNβ, suggesting that that the VSVmIFNβ mediated attrition was not overcome by depleting regulatory T cells or by providing homeostatic pro-survival cytokines (FIG. 1J).

Figure 2A:

Example 2—Oncolytic VSVmIFNβ Infection Promotes Attrition of WT but not IFNAR KO CAR T Cells in the Tumor and Spleen To quantify the magnitude of the CAR T cell attrition and to evaluate how it related to virus replication and cytokine and chemokine induction, a single dose of VSVmIFNβ was administered at time points ranging between 6 and 72 hours prior to adoptive transfer of CAR T cells (FIG. 2A). Three days post CAR administration, viable CAR T cells were enumerated in the tumor and in the spleen. Fewer viable CD8 and CD4 CAR T cells were recovered from tumors injected with VSVmIFNβ 6 or 24 hours prior to adoptive transfer. A similar reduction in the number of CAR T cells was observed in the spleen, and in combination with the results from blood (FIGS. 1E and 1I), these data suggested that the attrition was systemic and not due to mislocalization of CAR T cells.

As the most profound loss of CAR T cell occurred at the time points at which the peak concentration of IFNβ was observed in the tumor, studies were conducted to evaluate whether the attrition was intrinsic to the virus or largely due to the expression of the transgene. VSVmIFNβ or VSVGFP was administered 6 hours prior to CAR T cell transfer, and 18 hours later, viable CAR T cells were quantified in the tumor and the spleen (FIG. 2F). An attenuated attrition of CAR T cells was observed in the tumor, and there was no significant reduction in CAR T cell numbers in the spleen if VSV GFP was administered rather than VSVmIFNβ (FIGS.

2G and 2H). Moreover, the CAR T cell loss was inversely correlated with the magnitude of type I IFN induction in the tumor (FIG. 2I).

Type I IFNs can either promote or inhibit T cell activation, proliferation, differentiation, and survival, depending on the timing and concentration of exposure. Since the in vivo model suggested an inverse correlation between CAR T viability and type I IFN concentration in the tumor, studies were conducted to evaluate whether CAR T cells generated from donor mice that do not express the type I IFN receptor (IFNAR KO) would be protected from the deleterious effects induced by VSVmIFNβ (FIG. 2J). Contrary to the reduction in WT CD8 T CAR T cells in the tumor and the spleen observed in VSV infected tumors, a significantly reduced number of IFNAR KO CD8 CAR T cells was not detected in the tumor or the spleen (FIGS. 2K and 2L), thereby confirming the critical role of type I IFN in the VSVmIFNβ-mediated attrition.

Example 3—Type I IFN Promotes Dysregulated Expression of the CAR, Exhaustion, and Apoptosis To further evaluate the effect of type I on CAR T cells, in vitro culture systems of CAR T cells alone or CAR T cells co-cultured with target B16EGFRvIII tumor cells at an effector to target (E:T) ratio of 1:5 were evaluated in the presence or absence of recombinant IFNβ. Consistent with the in vivo loss of CAR T cells in VSVmIFNβ infected tumors, a dose-dependent increase in the proportion of AnnexinV positive apoptotic cells was observed (FIG. 3A). The type I IFN receptor signals through the Janus kinase (JAK)-signal transducer and activator of transcription (STAT) pathway, and inhibition of signal transduction with the Jak 1/2 inhibitor Ruxolitinib prevented the IFNβ induced increase in apoptosis. This effect was antigen independent, as it was observed both in the absence of EGFRVIII and in the presence of target expressing tumor cells (FIGS. 3A and 3B).

Figures 3E, 3F:
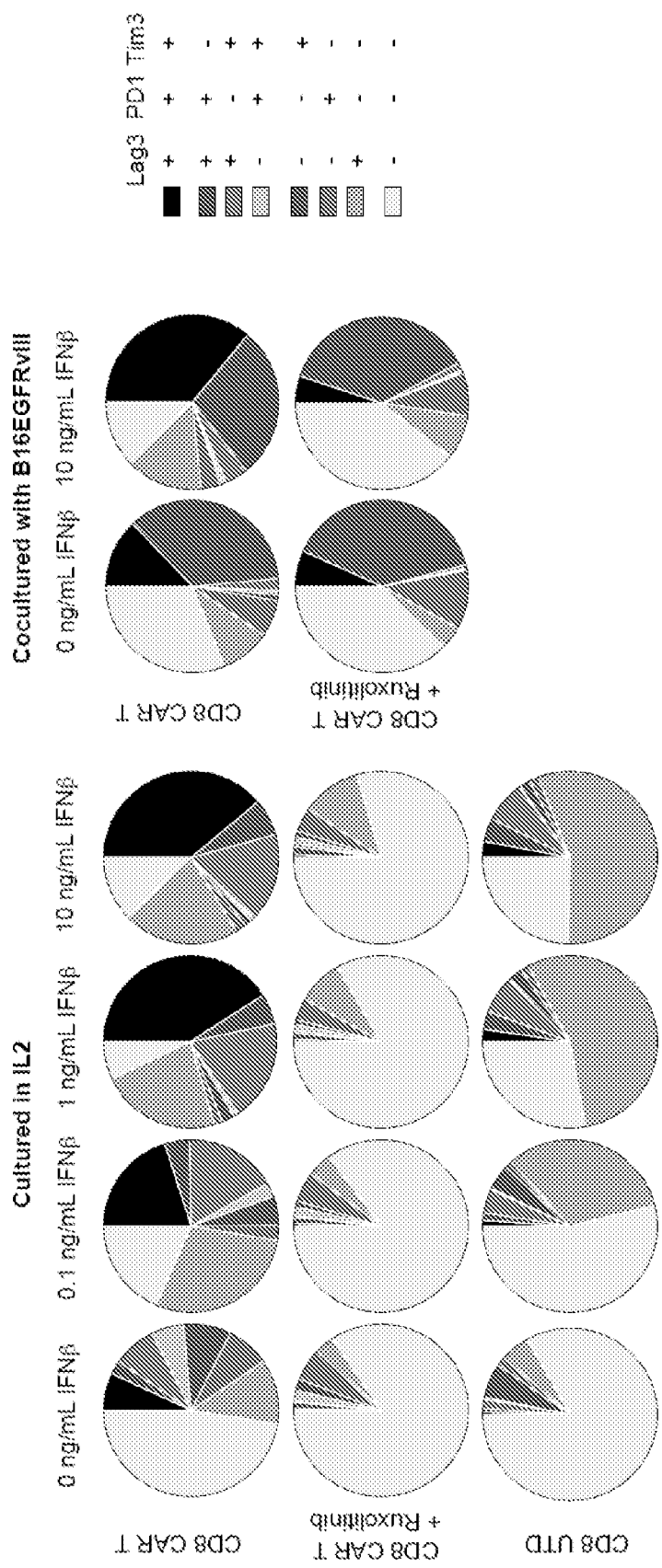
Figure 3H:
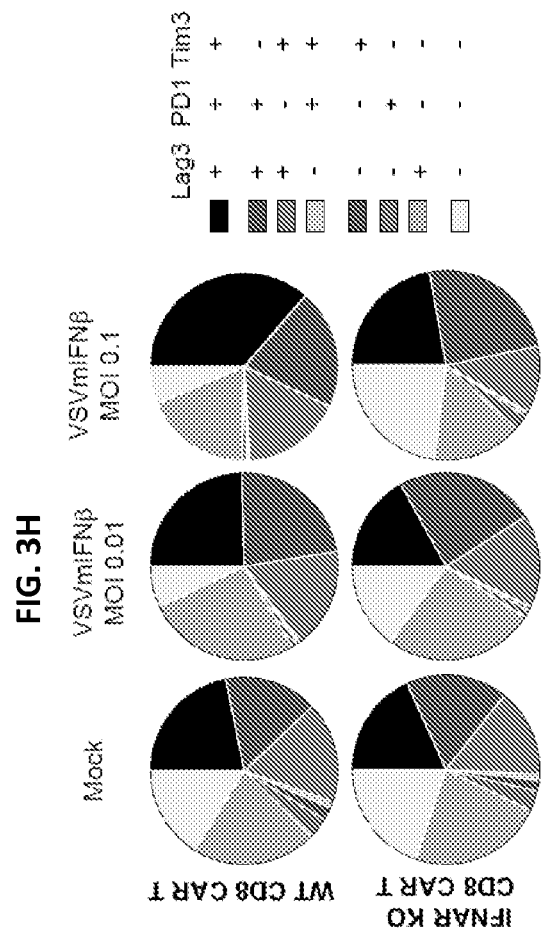
Figure 3G:
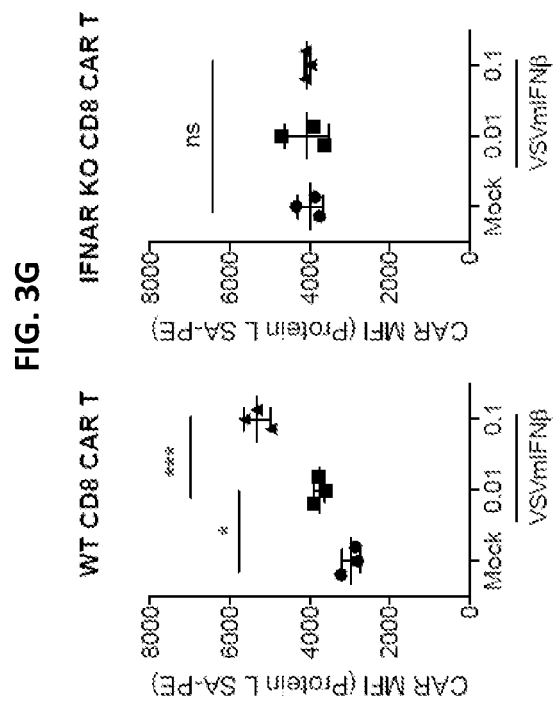

High level expression of the CAR molecule on T cells has been shown to sensitize them to tonic signaling, and to promote exhaustion and apoptosis (Long et al., Nat Med, 2015, 21(6):581-590); and Gomes-Silva et al., Cell Rep, 2017, 21(1): 17-26). Indeed, an IFNβ dose-dependent increase was observed in CAR expression on the surface of transduced CD8 T cells, and the increase was blocked by Jak1 inhibition (FIGS. 3C and 3D). Correspondingly, a dose dependent increase in expression of the exhaustion markers Lag3, PD1, and Tim 3 that was blocked by Jak1 inhibition was observed in transduced CD8 T cells, but not in untransduced CD8 T cells (FIGS. 3E and 3F). The proportion of triple positive cells was dramatically increased by IFNβ between 0 and 1 ng/mL, and plateaued at higher doses. To further confirm the effect of type I IFN on the dysregulated expression of the CAR and subsequent induction of exhaustion mechanisms, a co-culture system using mock infected or VSVmIFNβ infected B16EGFRVIII target tumor cells with CAR T cells at E:T ratio of 1:4 was employed. While CAR expression was enhanced on WT CD8 T cells co-cultured with infected tumor cells in a dose-dependent manner, no change was observed in surface expression of the CAR on the IFNAR KO CD8 T cells (FIG. 3G). Although the exhaustion profile of the IFNAR KO and WT CD8 CAR T cells was similar in the mock infected co-culture condition, WT CD8 CAR T cells exhibited an enhanced exhaustion profile in the presence of VSVmIFNβ infected tumor cells that was not observed in the IFNAR KO CD8 CAR T cells (FIG. 3H).

As with the EGFRVIII CAR, IFNβ promoted higher expression levels of the CAR molecule on the surface of CD19-specific CAR T cells and supported an activated phenotype. In contrast to the EGFRVIII CAR, however, the higher level of expression of the CD19-specific CAR was not associated with increased levels of inhibitory receptor expression over and above the T cell intrinsic IFNβ mediated changes observed in the untransduced cells (FIGS. 8A-C).

Example 4—Type I IFN Resistant CAR T Cells Provide Additive Therapy with VSVmIFNβ in Lymphodepleted Mice Since IFNAR KO CAR T cells were at least partially resistant to the VSVmIFNβ induced attrition in vivo, and also were resistant to CAR expression dysregulation in vitro, studies were conducted to determine whether type I IFN insensitive CAR T cells would provide superior tumor control in combination with VSVmIFNβ, as compared to CAR T cells generated from WT donor mice. Tumor control and overall survival were evaluated in both non-preconditioned and lymphodepleted mice that received EGFRVIII CAR T cell monotherapy or combination therapy with VSVmIFNβ (FIG. 4A). Although IFNAR KO CAR T cell single agent therapy provided a modest extension in survival that was similar to the combination arm in the non-preconditioned animals, a significantly reduced tumor growth rate and a striking extension of survival were observed in lymphodepleted mice that received both IFNAR KO CAR T cells and three doses of VSVmIFNβ (FIGS. 4B and 4C).

These studies indicate that VSVmIFNβ infection remodels the TME in complex ways that are both helpful and deleterious to CAR T cell therapy. However, CAR T cells can be manipulated to be resistant to those harmful effects, as demonstrated with type I IFN resistance, to fully capitalize on the complementary mechanisms of action of each platform.

The study of FIGS. 4A-C was continued for a longer follow up. Tumor control and overall survival in both non-preconditioned and lymphodepleted mice that received IFNAR KO EGFRVIII CAR T cell monotherapy or combination with VSVmIFNβ were evaluated (FIG. 5A). A reduced tumor growth rate and a significant extension of survival were observed in lymphodepleted mice that received both IFNAR1 KO CAR T cells and three doses of VSVmIFNβ as compared to those animals that only received IFNAR1 KO CAR T cells (FIG. 5B).

In the non-lymphodepleted setting, tumor outgrowth was similar in animals receiving CAR T cells with or without VSVmIFNβ. It was further confirmed that in lymphodepleted animals, IFNAR KO and WT CAR T cells provided similar tumor control in combination with PBS injections. IFNAR KO CAR T cells, however, provided a significant survival advantage over WT CAR T cells when combined with VSVmIFNβ (FIGS. 5C and 5D).

Example 5—CRISPR Genetic Disruption of IFNAR1

CRISPR Cas9 genetic disruption of the IFNAR1 was performed on CAR T cells. Nucleofection of two IFNAR1 targeted crRNA RNP complexes on the day following retroviral CAR transduction ablated IFNAR1 expression and generated CAR$^+$ IFNAR1 CD8 and CD4 populations with approximately 92 and 85% efficiency, respectively (FIG. 6A). The sequences for these mouse IFNAR1 targeted crRNAs were as follows:

Mm.Cas9.IFNAR1.1.AA:TCAGTTACACCATACGAA-TC (SEQ ID NO:1)

Mm.Cas9.IFNAR1.1.AB: GCTTCTAAACGTACTTCT-GG (SEQ ID NO:2)

CRISPR modified CAR T cells were functionally insensitive to the deleterious effects of recombinant IFNβ and did not upregulate Fas (FIG. 6B), the CAR (FIG. 6C), or inhibitory receptors (FIG. 6D). In vivo, IFNAR CRISPR modified CAR T cells provided the greatest tumor control in combination with VSVmIFNβ against subcutaneous B16EGFRvIII tumors (FIGS. 6E and 6F).

Example 6—CAR T Cells in Combination with Other Viral Vectors

To confirm that injection (e.g., intratumoral injection) of viruses other than VSV produce CAR T cell attrition, mice bearing subcutaneous B16OVA-CD19 tumors were treated with $10^7$ CD19-specific CAR T cells on day 7 post implantation and two doses of intratumoral (IT) phosphate buffered saline (PBS) or $5 \times 10^8$ pfu of replication defective Adenovirus expressing GFP (Ad-GFP) on days 14 and 17. CAR T cells in the tumor were enumerated on day 20. Fewer CD8 and CD4 CAR T cells were recovered from the tumors of mice that received Ad-GFP IT compared with PBS (FIGS. 7A and 7B).

These results demonstrate that viral infections generate interference with CAR T cells against various targets (e.g., CD19 and EGFRvIII) through the production of type I IFN and that IFNAR KO CAR T cells can be applicable to multiple targets and multiple viral platforms.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cancer, the method comprising administering to the mammal:
   (a) an oncolytic virus (OV), wherein the virus induces expression of type I interferon (IFN), and
   (b) genetically modified T cells with reduced expression of interferon-α/β receptors (IFNARs).

2. The method of claim 1, wherein said mammal is a human.

3. The method of claim 1, wherein said oncolytic virus is a rhabdovirus, reovirus, adenovirus, or herpes simplex virus.

4. The method of claim 3, wherein said oncolytic virus is a vesicular stomatitis virus or Maraba virus.

5. The method of claim 1, wherein said genetically modified T cells express a chimeric antigen receptor, and wherein said chimeric antigen receptor is expressed from a retroviral vector or a lentiviral vector, and wherein said chimeric antigen receptor targets a tumor-associated antigen.

6. The method of claim 1, wherein said genetically modified T cells comprise a retrovirus or lentivirus expressing an shRNA targeted to a nucleic acid encoding said IFNARs, or wherein said genetically modified T cells comprise a genomic deletion of a nucleic acid encoding said IFNARs.

7. The method of claim 6, wherein said IFNARs are IFNAR1 subunits or IFNAR2 subunits.

8. The method of claim 1, wherein said OV and said genetically modified T cells are administered to said mammal in an amount effective to kill tumor cells within said mammal, or to reduce metastasis of said tumor in said mammal.

9. The method of claim 1, wherein said cancer is selected from the group consisting of glioblastoma, pancreatic adenocarcinoma, cholangiocarcinoma, mesothelioma, melanoma, prostate cancer, breast cancer, ovarian cancer, liver cancer, colorectal cancer, and melanoma.

10. A method for treating a mammal having cancer, wherein said method comprises administering, to said mammal, (a) a viral vector, wherein said viral vector induces expression of type I interferon (IFN) within said mammal, and (b) genetically modified T cells with reduced expression of interferon-α/β receptors (IFNARs).

SEQUENCE LISTING

```
<160> NUMBER OF SEQ ID NOS: 2

<210> SEQ ID NO 1
<211> LENGTH: 20
<212> TYPE: DNA
<213> ORGANISM: Mus musculus

<400> SEQUENCE: 1
tcagttacac catacgaatc                                              20

<210> SEQ ID NO 2
<211> LENGTH: 20
<212> TYPE: DNA
<213> ORGANISM: Mus musculus

<400> SEQUENCE: 2
gcttctaaac gtacttctgg                                              20
```

11. The method of claim 10, wherein said mammal is a human.

12. The method of claim 10, wherein said viral vector is a rhabdovirus, reovirus, adenovirus, or herpes simplex virus.

13. The method of claim 12, wherein said viral vector is a vesicular stomatitis virus or Maraba virus.

14. The method of claim 10, wherein said genetically modified T cells express a chimeric antigen receptor.

15. The method of claim 14, wherein said chimeric antigen receptor is expressed from a retroviral vector or a lentiviral vector, and wherein said chimeric antigen receptor targets a tumor-associated antigen.

16. The method of claim 10, wherein said genetically modified T cells comprise a retrovirus or lentivirus expressing an shRNA targeted to a nucleic acid encoding said IFNARs, or wherein said genetically modified T cells comprise a genomic deletion of a nucleic acid encoding said IFNARs.

17. The method of claim 16, wherein said IFNARs are IFNAR1 subunits or IFNAR2 subunits.

18. The method of claim 10, wherein said viral vector and said genetically modified T cells are administered to said mammal in an amount effective to kill tumor cells within said mammal, or in an amount effective to reduce metastasis of said tumor in said mammal.

19. The method of claim 10, wherein said cancer is selected from the group consisting of glioblastoma, pancreatic adenocarcinoma, cholangiocarcinoma, mesothelioma, melanoma, prostate cancer, breast cancer, ovarian cancer, liver cancer, colorectal cancer, and melanoma.

20. The method of claim 10, wherein said method further comprises administering a lymphodepleting regimen to said mammal.

* * * * *

UNITED STATES PATENT AND TRADEMARK OFFICE
CERTIFICATE OF CORRECTION

PATENT NO. : 12,121,554 B2
APPLICATION NO. : 17/275713
DATED : October 22, 2024
INVENTOR(S) : Laura Evgin, Richard G. Vile and Luis Sanchez-Perez Page 1 of 1

It is certified that error appears in the above-identified patent and that said Letters Patent is hereby corrected as shown below:

On the Title Page

Column 1 (Applicants), Lines 4-7, after (US);, delete "Laura Evgin, Rochester, MN (US); Richard G. Vile, Rochester, MN (US); Luis Sanchez-Perez, Apex, NC (US)".

Column 2 (Other Publications), Line 8, delete "Challeng"," and insert -- Challenge," --.

In the Claims

In Column 18, Line 16, In Claim 5, delete "receptor, and" and insert -- receptor, --.

Signed and Sealed this
Tenth Day of December, 2024

Katherine Kelly Vidal
*Director of the United States Patent and Trademark Office*